United States Patent [19]

Endo et al.

[11] Patent Number: 5,354,995
[45] Date of Patent: Oct. 11, 1994

[54] SUBSTRATE DETECTING DEVICE FOR DETECTING THE PRESENCE OF A TRANSPARENT AND/OR AN OPAQUE SUBSTRATE BY OUTPUT OF JUDGEMENT MEANS

[75] Inventors: Shunetsu Endo; Mitsuo Kato, both of Sagamihara; Masato Asakawa, Machida, all of Japan

[73] Assignees: Tokyo Electron Kabushiki Kaisha, Tokyo; Tokyo Electron Tohoku Kabushiki Kaisha, Esashi, both of Japan

[21] Appl. No.: 109,430

[22] Filed: Aug. 20, 1993

[30] Foreign Application Priority Data

Aug. 24, 1992 [JP] Japan ................................. 4-247304

[51] Int. Cl.⁵ ............................................. G01N 21/86
[52] U.S. Cl. .................................. 250/561; 250/223 R; 414/331
[58] Field of Search ............... 250/559, 561, 571, 221, 250/222.1, 223 R; 414/331, 937

[56] References Cited

U.S. PATENT DOCUMENTS

| | | | |
|---|---|---|---|
| 4,540,887 | 9/1985 | Minerd et al. | 250/561 |
| 5,194,743 | 3/1993 | Aoyama et al. | 250/561 |
| 5,225,691 | 7/1993 | Power et al. | 414/331 |
| 5,239,182 | 8/1993 | Tateyama et al. | 414/331 |

FOREIGN PATENT DOCUMENTS

| | | | |
|---|---|---|---|
| 0071794 | 4/1988 | Japan | 250/561 |
| 0201506 | 8/1988 | Japan | 250/561 |

Primary Examiner—David C. Nelms
Assistant Examiner—Stephone B. Allen
Attorney, Agent, or Firm—Beveridge, DeGrandi, Weilacher & Young

[57] ABSTRACT

A device for detecting a semiconductor wafer in a non-contact manner irrespective of transparency or opacity thereof. At positions corresponding to a plurality of wafers loaded on a carrier, a plurality of light emitting-/receiving sensors and a plurality of light receiving sensors are correspondingly provided in pairs in such a manner that their respective light emitting/receiving surfaces and their respective light receiving surface in pairs confront each other. The light emitting/receiving sensors and light receiving sensors are alternately arranged in two rows lengthwise on a sensor support board. In the case of a transparent wafer, a light sent out from a light emitting section of the light emitting-/receiving sensor strikes on and is reflected by the surface of the wafer. The thus reflected light is then detected by a light receiving section of the same light emitting/receiving sensor. In the presence of an opaque wafer, a light sent out from the light emitting/receiving sensor is not permitted to reach the confronting light receiving sensor. Conversely, in the absence of the opaque wafer, the light reaches the light receiving sensor for detection. On the other hand, there is provided a judgment section switchably inputting one of a light reception signal generated at the light receiving section of the light emitting/receiving sensor and a light reception signal generated at the light receiving section of the light receiving sensor.

10 Claims, 5 Drawing Sheets

SUBSTRATE DETECTING DEVICE FOR DETECTING THE PRESENCE OF A TRANSPARENT AND/OR AN OPAQUE SUBSTRATE BY OUTPUT OF JUDGEMENT MEANS

BACKGROUND OF THE INVENTION

The present invention relates to a device for detecting a substrate such as a semiconductor wafer, intended to be used in a semiconductor device fabrication system.

In a typical process for fabricating semiconductor devices, for the purpose of introducing wafers into treatment sections such as heat treatment chambers, a container carrying untreated wafers (which in general is called a "carrier" or a "cassette") is commonly conveyed by way of an inlet/outlet port into an intermediate chamber, where the wafers are taken out from the carrier by means of a conveying mechanism such as arms for the conveyance into one of the treatment chambers. The carrier has an open bottom as known, and includes on each side thereof comb-teeth-like guide grooves extending in parallel to correspondingly guide and receive the lateral edges of the wafers so as to accommodate, for example, twenty-five wafers.

In order to control the conveying action of the conveying mechanism or to perform a control within the treatment chamber, detection must be made of the presence or absence of the wafers resting between the opposite guide grooves in the carrier placed at the inlet/outlet port. To this end, a wafer counter is provided.

Due to the opacity of silicon wafers which are generally in use as semiconductor wafers, there has been hitherto used a wafer counter of a transmission type having a light emitting section comprised of a light emitting diode and a light receiving section comprised of a photo-transistor arranged respectively on one side and the other side of respective regions where the wafers are disposed, the presence or absence of the wafers being detected based on light reception signals derived from the light receiving section.

However, there have been lately manufactured transparent quartz wafers consisting of LCD substrates in array. Such transparent wafer substantially transmits therethrough light sent out from the light emitting section, and hence the conventional transmission type wafer counter cannot detect whether a transparent wafer is present or absent. This is due to the following fact. In the presence of the transparent wafer, the amount of light received by the light receiving section slightly reduces since a small amount of light is absorbed by the transparent wafer. Nevertheless, the light receiving section receives the light from the light emitting section irrespective of the presence or absence of the wafer. The range of output voltage levels corresponding to various light receiving states has a certain width (due to, for example, unevenness in characteristics of the photo-transistors, or influence of the disturbance light), and there is only a slight difference in light receiving amount between the "presence" and "absence". It is therefore very difficult and virtually impossible to electrically distinguish the difference.

For this reason, there can be used a method of detecting the presence or absence of the transparent wafer with the aid of microswitches or the like. Since a contact type is employed in this case, the microswitches may possibly contaminate the wafers, or damage the peripheries of the wafers.

SUMMARY OF THE INVENTION

The present invention was conceived in view of these circumstances, and its object is to provide a substrate detecting device capable of detecting the presence or absence of substrates in a non-contact manner even when transparent substrates are contained among the substrates to be treated.

According to the present invention, the above object can be accomplished by a substrate detecting device comprising light emitting means provided on the side of one surface of a substrate to be disposed in a region where the substrate is arranged, the emitting means being provided to emit a light toward the one surface; first light receiving means positioned on a path of a light emitted from the light emitting means and, if a transparent substrate is disposed in the region, reflected by the one surface of the transparent substrate; first judgment means for judging the presence or absence of the transparent substrate based on a reception signal transmitted from the first light receiving means; second light receiving means provided on the side of the other surface of the substrate to be disposed in the region; the second light receiving means being provided to receive a light from the light emitting means which has advanced through the region; and second judgment means for judging the presence or absence of an opaque substrate based on a light reception signal transmitted from the second light receiving means.

For instance, a pulse voltage is applied to the light emitting means to cause the latter to perform a pulsing light emission. Based on a light reception signal transmitted from the light receiving means and corresponding to a reflection light of the pulsing light, the judgment means judges the presence or absence of the transparent substrate. When the transparent substrate is absent in its loading region, the first light receiving means is not allowed to receive a light sent out from the light emitting means, whereas when it is present in the loading region, the first light receiving means is permitted to receive a light from the light emitting means. Thus, by presetting a judgment level between two voltage levels corresponding to the presence or absence of a light reception, it can be judged whether the transparent substrate is present or absent. The second light receiving means is not permitted to receive a light from the light emitting means when the opaque substrate is present, whereas it receives the light if absent, thus judging the presence or absence of the opaque substrate. Consequently, the substrate detecting device of the present invention makes it possible to detect both the transparent substrate and the opaque substrate.

DESCRIPTION OF THE PREFERRED EMBODIMENTS

Figure 1:
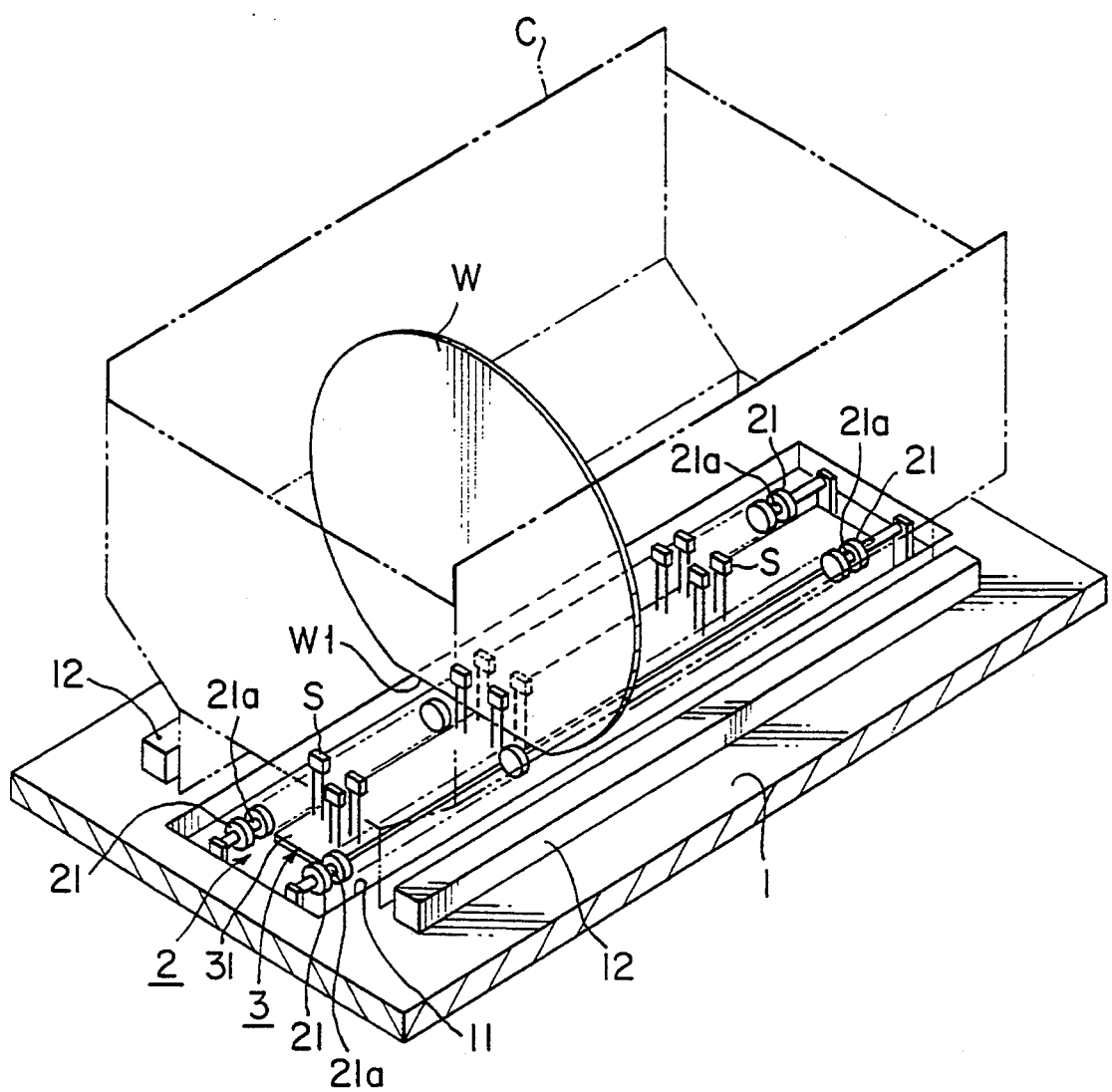
FIG. 1 is a schematic perspective view of an embodiment of a substrate detecting device in accordance with the present invention.

FIG. 1 is a schematic perspective view showing an embodiment of a substrate detecting device constructed in accordance with the present invention and being used as a wafer counter. Referring to FIG. 1, there is shown a carrier mounting table designated at 1 and including at its center a rectangular cutout 11. The carrier mounting table 1 further includes along the two sides of the cutout 11 a pair of guide rails 12 for positioning a wafer carrier C described later. The carrier mounting table 1 is placed, for example, at an inlet/outlet port of a wafer heat treatment furnace. FIG. 1 depicts a state where the carrier C accommodating therein, for example, twenty-five wafers W and having an open bottom is guided by the guide rails 12 and positioned therebetween.

The interior region of the rectangular cutout 11 carries along confronting long sides thereof a pair of elongated rollers 21. In a known manner by virtue of an elevator not shown, there is vertically displaceably provided a known orientation flat aligner 2 which serves to orient an orientation flat W1 of a wafer W to a predetermined direction through the rotation of the pair of rollers 21. At regular intervals in its longitudinal direction, the roller 21 includes a series of circumferentially formed grooves 21a whose number is, for example, twenty-five corresponding to the number of wafers W to be accommodated, thereby guiding the periphery of each of the wafers W resting within the carrier C.

Figure 2:
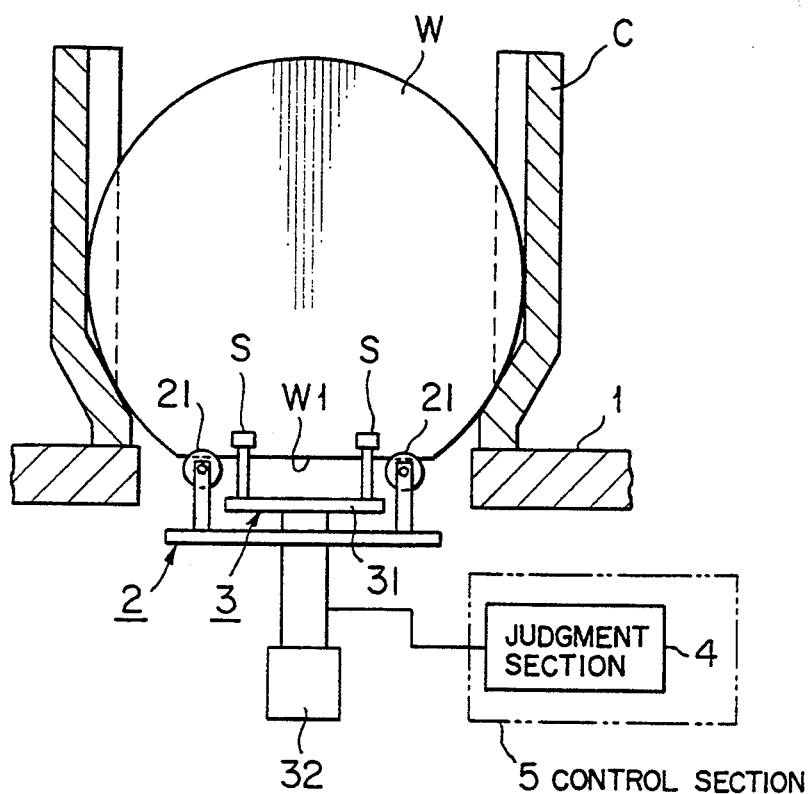
FIG. 2 is an elevational view in vertical section, showing a major part of the embodiment in FIG. 1.

Between the pair of rollers 21 of the orientation flat aligner 2, there is interposed a wafer counter 3 for counting the number of the wafers being carried within the carrier C. As is shown in FIG. 2, the wafer counter 3 comprises a sensor support board 31, an elevator 32 for elevating the sensor support board 31 while bearing it from below, a plurality of sensors S arranged on each side of the top surface of the sensor support board 31 along the direction in which the wafers are arranged, and a judgment section 4 described later for judging the presence or absence of the wafers based on signals received from the sensors S. It is to be noted that the judgment section 4 is provided within a control section 5 for controlling the overall system on the basis of, for example, the results of measurement performed by the wafer counter 3.

Figure 3A:
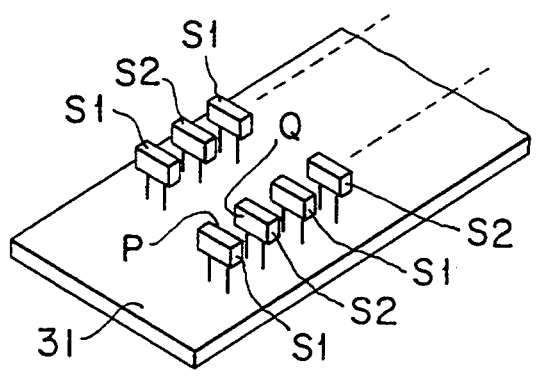
FIG. 3A is a perspective view showing an arrangement of substrate detecting sensors depicted in FIG. 1.
Figure 3B:
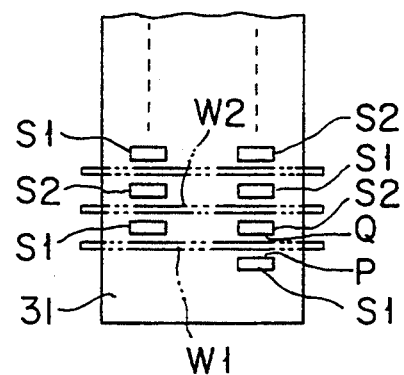
FIG. 3B is a top plan view of FIG. 3A.

As is apparent from FIGS. 3A and 3B, the sensors S comprises two types of sensors, that is, light emitting/receiving sensors S1 each having a light emitting section and a light receiving section in an adjoining manner, and light receiving sensors S2 each having only a light receiving section. For each of the rows of the sensors, the light emitting/receiving sensor S1 and the light receiving sensor S2 are alternately arranged.

Description will now be given of a relationship in arrangement of the sensors S (S1, S2) and the wafers W within the carrier C. Turning to FIGS. 3A and 3B, as viewed from this side, in the right row the light emitting/receiving sensor S1 and the light receiving sensor S2 are alternately arranged in the mentioned order from this side, whereas in the left row the light emitting/receiving sensor S1 and the light receiving sensor S2 are arranged by turns in the mentioned order starting from a position adjacent to the position obtained by shifting the first sensor S in the right row by one to the far side (in other words, from a position adjacent and corresponding to the position of the light receiving sensor S2 which is the second sensor S in the right row). More specifically, when viewed from this side in FIGS. 3A and 3B, the light emitting/receiving sensor S1 has at its rear side a light emitting/receiving surface P (consisting of a light emitting surface of the light emitting section and a light receiving surface of the light receiving section), while the light receiving sensor S2 has at its front side a light receiving surface Q. The sensors S1 and S2 are positioned in pairs (S1, S2) in such a manner that the light emitting/receiving surface P and the light receiving surface Q confront each other to detect the presence or absence of the wafer W.

Thus, as seen in FIG. 3B, by way of example, the first wafer W1 when viewed from this side can be detected by the first sensor pair S1 and S2 in the right row, and the second wafer W2 can be detected by the first sensor pair S1 and S2 in the left row. The light emitting section of the light emitting/receiving sensor S1 is positioned adjacent to each of regions where the wafers W are disposed, more specifically in this example, so as to face one side of each of the regions accommodating the wafers W within the carrier C, whereas the light receiving section of the light emitting/receiving sensor S1 is so positioned as to lie on a path of light emitted from the light-emitting section thereof and reflected by the surface of each of the wafers W resting within the carrier C. The light receiving section of the light receiving sensor S2 is positioned on a path of incident light emitted from the light emitting section of the light emitting/receiving portion S1 so as to confront the light emitting portion by way of the wafer accommodation region. In this embodiment, the light receiving section of the light emitting/receiving sensor S1 constitutes a first light receiving means, while the light receiving section of the light receiving sensor S2 constitutes a second light receiving means.

Figure 4:
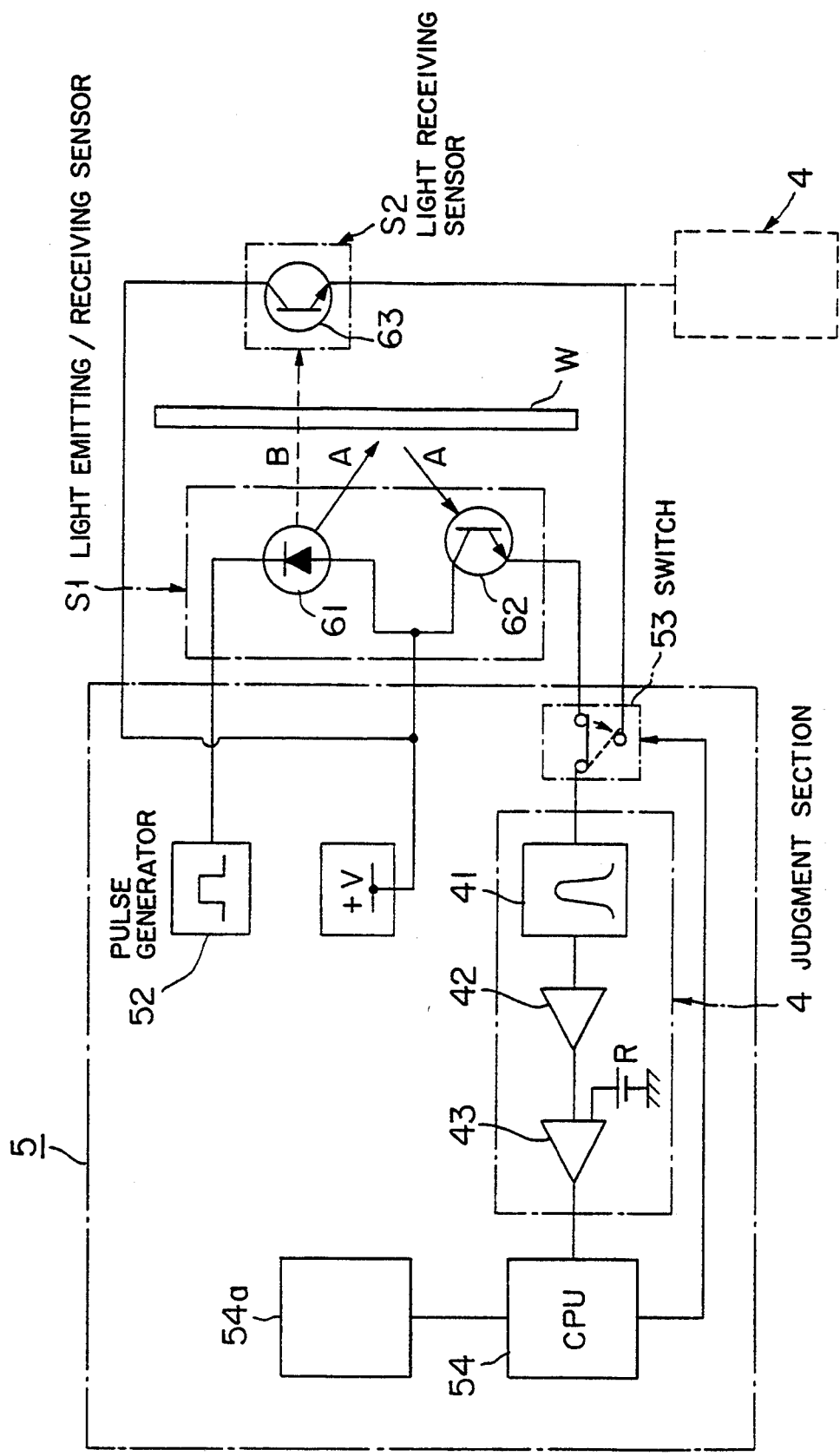
FIG. 4 is a diagram showing a substrate detecting circuit.

Referring next to FIG. 4, description will be given of configurations of the light emitting/receiving sensor S1 and the light receiving sensor S2, and of a wafer detecting circuit in the wafer counter 3 incorporating the same.

The light emitting/receiving sensor S1 comprises a light emitting diode 61 constituting the light emitting means, and a phototransistor 62 constituting the first light receiving means. The light receiving sensor S2 comprises a phototransistor 63 constituting the second light receiving means. The anode of the light emitting diode 61 and the collector of the phototransistor 62 are connected with each other in the light emitting/receiving sensor S1 to form a connection point which is in turn connected to a power supply 51 having a voltage of +V. The cathode of the light emitting diode 61 is connected to a pulse generator 52. The collector of the phototransistor 63 in the light receiving sensor S2 is also connected to the power supply 51.

On the other hand, the judgment section 4 comprises a band-pass filter 41 having a center frequency of, for example, 40 kHz, and a comparator 43 being connected to the output of the filter 41 via an amplifier 42. A CPU 54 is connected to the output of the judgment section 4. The comparator 43 is subjected to a preset voltage R. In this example, the circuits of the judgment section 4 are incorporated into a single operational amplifier. The emitters of the phototransistors 62 and 63 are connected by way of a switch 53 to the input of the judgment section 4 (more precisely, the input of the band-pass filter 41). In response to control signals transmitted from the CPU 54, the switch 53 functions to connect the input of the judgment section 4 to the phototransistor 62 in the mode of detecting the presence or absence of a transparent quartz wafer, whereas it allows the input of the judgment section 4 to be connected to the phototransistor 63 in the mode of detecting the presence or absence of an opaque silicon wafer.

The wafer counter 3 in accordance with the above-described embodiment includes twenty-five switches 53 so as to correspond to twenty-five pairs of sensors S1 and S2, thereby ensuring that output signals from the emitters of the phototransistors 62 (or 63) are sequentially supplied into the judgment section 4 by way of respective switch circuits not shown.

A function of the above embodiment will be described below. As shown in FIGS. 1 and 2, the carrier C loaded with the wafers W is first mounted on the carrier mounting table 1. The orientation flat aligner 2 is then raised by an elevator not shown up to a predetermined position where the pairs of rollers 21 are rotated to orient the orientation flats of the wafers W to a predetermined direction. Afterwards, the orientation flat aligner 2 is lowered while the wafer counter 3 is raised to a predetermined level by means of the elevator 32.

In case of judging the presence or absence of a transparent substrate, for example, a transparent quartz wafer W, the switch 53 is changed over as indicated by a solid line in response to control signals transmitted from the CPU 54, thereby electrically connecting the phototransistor 62 to the judgment section 4, while the pulse generator 52 is put in motion to cause the light emitting diode 61 to give out light in a pulsing manner.

When a transparent quartz wafer W intervenes between the sensors S1 and S2, that is, when it is placed on an loading position corresponding to a particular sensor pair S1 and S2 within the carrier C, a part of a light sent out from the light emitting diode 61, for example, approximately 4% thereof, is reflected on the surface of the wafer W as indicated by a solid line arrow A in FIG. 4 and received by the phototransistor 62. As a result, in response to the above-mentioned pulsing light emission, the phototransistor 62 produces a pulse current which in turn correspondingly establishes a pulse voltage. The pulse voltage is input through the bandpass filter 41 and the amplifier 42 into the comparator 43. As the input voltage exceeds the preset voltage R, the comparator 43 is turned on. Conversely, in the absence of the transparent quartz wafer W, the phototransistor 62 does not receive any light from the light emitting diode 61. Thus, the pulse voltage is not introduced into the judgment section 4, and therefore the comparator 43 is left off. In this manner, the CPU 54 receives detection results in sequence from the sensors S1 resting e.g., at one end of the sensor board 31, thereby making it possible to detect whether the wafer W is present or absent at each loading position within the carrier C, in other words, to count the number of the wafers loaded on the carrier C.

On the contrary, for the judgment of the presence or absence of an opaque substrate, for example, a silicon wafer W, the switch 53 is changed over as indicated by a broken line in FIG. 4 in compliance with a signal derived from the CPU 54, so that the phototransistor 63 can be electrically connected to the judgment section 4. Thus, based on the light reception signals from the phototransistor 63, the judgment section 4 judges in the same manner whether the opaque silicon wafer W is present or absent.

In this case, providing that the opaque wafer W is absent, the phototransistor 63 is allowed to receive a pulse light from the light emitting diode 61 as indicated by a broken line arrow B in FIG. 4 to thereby turn the comparator 43 on. Conversely, providing that the silicon wafer W is present, the phototransistor 63 is not permitted to receive a pulse light therefrom, and hence the comparator 43 remains off. Thus, through the adoption of opposite recognition to the case of detecting a transparent quartz wafer W, the CPU 54 is similarly capable of counting the number of the wafers lying within the carrier C also in the case of detecting a silicon wafer W.

How a wafer is detected in case it is unknown whether the wafer is transparent or opaque will be described with reference to FIG. 8. First the switch 53 is changed over to the solid line position in FIG. 4, and the presence or absence of a wafer is detected by the phototransistor 62. If a wafer is detected by the phototransistor 62, it is determined that there is a transparent wafer. If a wafer is not detected by the phototransistor 62, it must be determined whether there is no wafer or whether there is an opaque wafer. For this purpose, the switch 53 is changed over to the broken line position in FIG. 4 for the detection by the phototransistor 63. If a wafer is detected by the phototransistor 63, it means that there is an opaque wafer, while if a wafer is not detected by the phototransistor 63, it means that there is neither a transparent wafer nor an opaque wafer.

Figure 8:
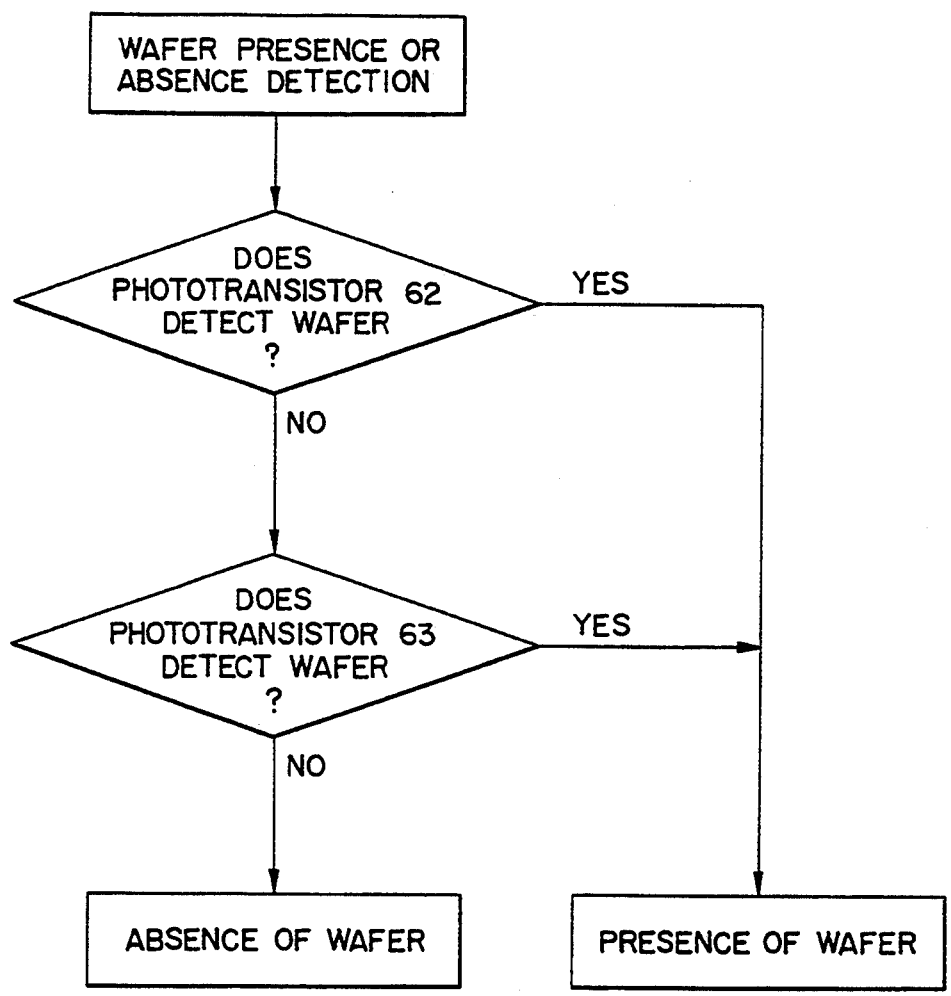
FIG. 8 is a flowchart of control to be executed in the substrate detecting circuit depicted in FIG. 4.

Therefore, in the case where it is not known whether wafers to be detected are transparent or opaque, a storage unit 54a may be connected to the CPU 54 as indicated in FIG. 4 to automatically execute the steps shown in FIG. 8. Then, the judgement can be automatically made even in case where it is unknown whether wafers are transparent or opaque.

Figure 5:
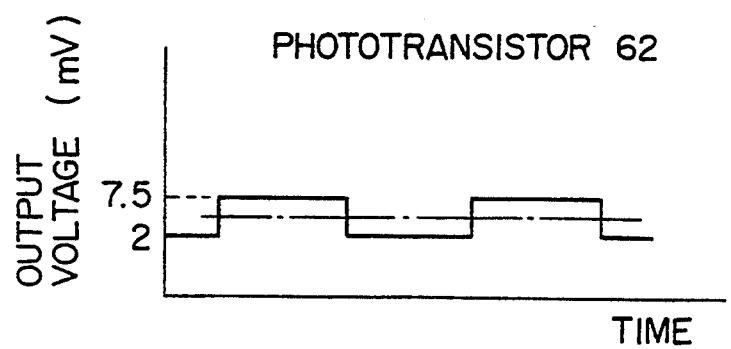
FIG. 5 is a graph showing an output waveform derived from a phototransistor constituting a light emitting/receiving sensor, which waveform appears at the time of detecting a transparent substrate.

In order to detect the presence or absence of the transparent quartz wafer W, according to such embodiment, use is made of a light reflected by the surface of the wafer W, and it has only to be electrically recognized whether the phototransistor 62 receives the light from the light emitting diode 61 or not. Therefore, the phototransistor 62 presents a large fall in its output voltage as shown in FIG. 5, for example, thereby ensuring a secure detection as to whether the wafer W is present or absent. Furthermore, irrespective of the transparency or the opacity of the wafer W, it can be detected whether the wafer W is present or absent without bringing the sensors into contact with the wafer W if present, to thereby prevent particles from adhering onto the wafer W.

Figure 6:
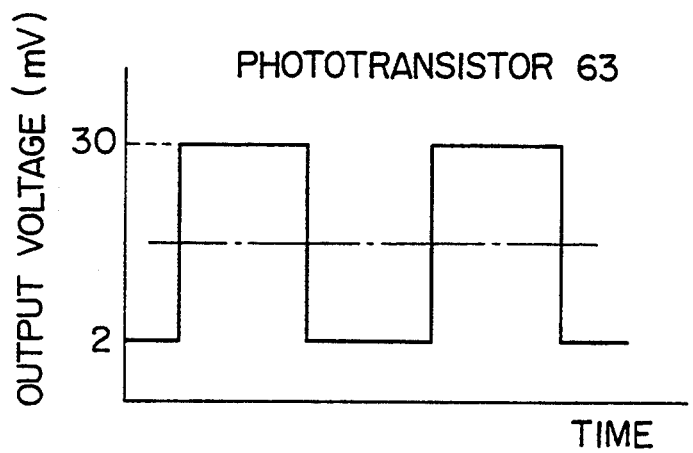
FIG. 6 is a graph showing an output waveform derived from a phototransistor constituting a light receiving sensor, which waveform appears at the time of detecting an opaque substrate.

Referring now to FIGS. 5 and 6, there are shown, by way of example, an output waveform obtained from the phototransistor 62 in the presence of the transparent quartz wafer, and an output waveform obtained from the phototransistor 63 in the absence of the opaque silicon wafer, respectively. As is apparent from FIGS. 5 and 6, the phototransistor 62 exhibits an output level of 7.5 mV when receiving a light reflected by the transparent quartz wafer, whereas the phototransistor 63 presents an output level of 30 mV when directly receiving a light from the light emitting diode 61, with 2 mV output level in the case of the phototransistors 62 and 63 not receiving any light therefrom. In this example, therefore, a common judgment section has applications to both the phototransistors 62 and 63 if a certain voltage between 2 and 7 mV is compared with the output voltage derived from the phototransistors 62 and 63.

In the present invention, first and second judgment sections 4 may be associated with the light reception signals derived from the phototransistors 62 and 63, respectively, as indicated by a broken line in FIG. 4, although they may be naturally integrated into a single judgment section in common as in the above embodiment.

The wafer counter in accordance with the above-described embodiment is provided with the light emitting/receiving sensor S1 and the light receiving sensor S2 so as to enable both the transparent wafer W and the opaque wafer W to be detected.

Figure 7:
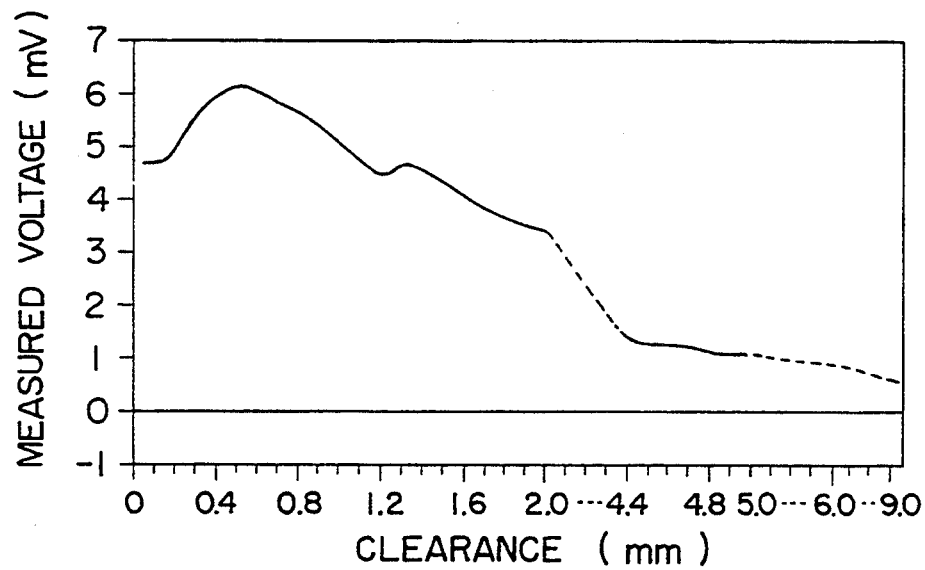
FIG. 7 is a graph showing a relationship between an output voltage of the phototransistor and a clearance between the light emitting/receiving sensor and the transparent substrate.

Referring now to FIG. 7, there is shown a relationship between an output voltage arising from the phototransistor 62 and a clearance between the light emitting diode 61 and a transparent quartz wafer having a reflectivity of 4%. As is apparent from the graph, the output voltage originated from the phototransistor 62 remarkably drops when the clearance is larger than 4 mm, which may prevent a secure recognition of the transparent wafer. Thus, the clearance should lie preferably within a range of 0 to 4 mm, and more preferably within a range of 0.7 to 2.5 mm in particular. The reason why the preferred lower limit is 0.7 mm is that if the light receiving section is positioned in close proximity of a wafer loading region the former may adversely receive a light reflected by the next wafer in spite of the absence of the wafer there. It will be appreciated that the difference in measurement values in FIGS. 5 and 7 (the output level is 7.5 mV in FIG. 5, whereas it is 6.2 mV in FIG. 7) is caused by the use of different measuring instruments. More specifically, the data shown in FIG. 5 represent a peak value measured by means of an oscilloscope, while the data shown in FIG. 7 are effective values of a pulse wave measured by a digital tester.

It is to be noted that the transparent substrate is not limited to the quartz wafer and may comprise, for example, a transparent plastic substrate. A certain opaque substrate is also available. Naturally, the reflectivity of the transparent substrate is not limited to 4%. Moreover, the opaque substrate is not limited to the silicon wafer, and may comprise any other opaque substrate. The present invention is not limited to the application to the wafer counter, and is applicable to other apparatus.

Description will now be given of a transfer of the wafers and the conveyance of the carrier. As the wafer and carrier are made of insulating materials, they may be charged with electricity due to, for example, a dry air flow, and may allow an abrupt electric current therethrough when coming into contact with a metallic conveying arm or the like, which may adversely influence the wafer. It is therefore desirable that the means for conveying the wafer or the carrier be comprised of a resistor having the same resistivity as that of the semiconductor. For example, the wafer and carrier have a capacitance of the order of 100 pF with a charged voltage of 20 kV, whose amount of electric charge results in 2μ coulomb in this state. Therefore, the use of the resistor of 1M Ω enables the electric discharge to be completed in 0.1 msec with the electric current of 20 mA, thus obviating the adverse influence onto the wafer.

According to the present invention, the substrate detector is capable of detecting whether the substrate is present or absent in a non-contact manner without coming into contact with the substrate to be detected, thereby ensuring a secure detection of the presence or absence of the substrate, free from the risk of adhesion of particles onto the substrate and the risk of damaging the substrate. Furthermore, the present invention enables the same detecting device to be used in detecting the presence or absence of both the transparent substrate and the opaque substrate.

What is claimed is:

1. A substrate detecting device comprising:
   light emitting means provided on the side of one surface of a substrate to be disposed in a region where said substrate is arranged, said emitting means being provided to emit a light toward said one surface;
   first light receiving means positioned on a path of a light emitted from said light emitting means and, if a transparent substrate is disposed in said region, reflected by said one surface of the transparent substrate;
   first judgment means for judging the presence or absence of said transparent substrate based on a reception signal transmitted from said first light receiving means;
   second light receiving means provided on the side of the other surface of said substrate to be disposed in said region; said second light receiving means being provided to receive a light from said light emitting means which has advanced through said region; and
   second judgment means for judging the presence or absence of an opaque substrate based on a light reception signal transmitted from said second light receiving means.

2. A substrate detecting device according to claim 1, wherein said first and second judgment means comprise a common single judgment means.

3. A substrate detecting device according to claim 1, wherein said light emitting means and said first light receiving means are adjacently combined into a single light emitting/receiving sensor.

4. A substrate detecting device according to claim 3, wherein said second light receiving means comprises a light receiving sensor arranged opposite to said light emitting/receiving sensor.

5. A substrate detecting device according to claim 4, further comprising a sensor support board, wherein:
   said sensor support board includes thereon a plurality of regions where a plurality of substrates are correspondingly disposed, and wherein:
   said light emitting/receiving sensor and said light receiving sensor are provided in pairs on the sides of said one surface and said other surface, respectively, of the substrate disposed in each of said regions, and wherein:
   two sensor pairs located in any two adjacent ones of said regions are separately arranged on different sides on said sensor support board.

6. A substrate detecting device according to claim 1, further comprising:

a pulse generator connected to said light emitting means so that the latter can perform a pulsing light emission.

7. A substrate detecting device according to claim 1, wherein:

said light emitting means comprises a light emitting diode, and wherein:

said first and second light receiving means comprise first and second phototransistors.

8. A substrate detecting device according to claim 7, wherein:

said pulse generator is connected to the cathode of said light emitting diode, and wherein:

the anode of said light emitting diode and the collectors of said first and second phototransistors are connected to a power supply, and wherein:

the emitters of said first and second phototransistors are connected to said first and second judgment means, respectively.

9. A substrate detecting device according to claim 8, wherein:

said first and second judgment means comprise a common single judgment means, and wherein:

the emitters of said first and second phototransistors are connected to said common judgment means by way of a changeover switch.

10. A substrate detecting device according to claim 1, wherein:

said judgment means comprises a band-pass filter, and a comparator provided to receive an output from said band-pass filter and to produce an output when the output is larger than a preset value.

* * * * *